United States Patent
Samoocha et al.

(10) Patent No.: US 9,393,389 B2
(45) Date of Patent: Jul. 19, 2016

(54) SELF CLEANING SHUNT

(75) Inventors: Or Samoocha, Acco (IL); Menashe Zaaroor, Tiberias (IL); Moshe Shoham, Hoshaya (IL)

(73) Assignee: Technion Research & Development Foundation Ltd., Haifa (IL)

( * ) Notice: Subject to any disclaimer, the term of this patent is extended or adjusted under 35 U.S.C. 154(b) by 782 days.

(21) Appl. No.: 13/805,041

(22) PCT Filed: Jun. 19, 2011

(86) PCT No.: PCT/IL2011/000486
§ 371 (c)(1),
(2), (4) Date: Mar. 4, 2013

(87) PCT Pub. No.: WO2011/158244
PCT Pub. Date: Dec. 22, 2011

(65) Prior Publication Data

US 2013/0158464 A1    Jun. 20, 2013

Related U.S. Application Data

(60) Provisional application No. 61/344,251, filed on Jun. 18, 2010.

(51) Int. Cl.
*B08B 9/00*    (2006.01)
*A61M 27/00*    (2006.01)
(Continued)

(52) U.S. Cl.
CPC .............. *A61M 27/006* (2013.01); *B08B 9/027* (2013.01); *A61M 2025/0019* (2013.01)

(58) Field of Classification Search
CPC ....... B08B 9/027; B08B 9/00; A61M 1/3655; A61M 2025/0019; A61M 2025/0086; A61M 2025/0087

USPC ....................................................... 15/104.05
See application file for complete search history.

(56) References Cited

U.S. PATENT DOCUMENTS 4,698,058 A    10/1987  Greenfeld et al.
4,725,207 A    2/1988   Buchwald et al.
(Continued)

FOREIGN PATENT DOCUMENTS

JP       03-029665        2/1991
WO    WO2008/126087 A2   10/2008

OTHER PUBLICATIONS

PCT Search Report dated Dec. 12, 2011 of Patent Application No. PCT/IL11/00486 filed Jun. 19, 2011.
(Continued)

*Primary Examiner* — David Redding
(74) *Attorney, Agent, or Firm* — Maine Cernota & Rardin

(57) ABSTRACT

A self cleaning inlet head for use on a shunt. The head has a tube with openings disposed in predetermined positions in its wall, and a cleaning element installed inside the tube. The cleaning element may comprise a central shaft with a number of bristles protruding therefrom, preferably in locations substantially identical to the positions of the openings in the wall of the tube. Mutual vibratory motion between the cleaning element and the tube causes at least some of the bristles to enter the openings, thereby keeping them clear, and preventing tissue growth into them. The vibratory motion may be generated by the action of an external field on a responsive part of the cleaning element, such as an external magnetic field operating on a magnetic or magnetized part of the cleaning element or the bristles. Alternatively, the external field may be an ultrasound field operating on the bristles.

12 Claims, 3 Drawing Sheets

(51) Int. Cl.
*B08B 9/027* (2006.01)
*A61M 25/00* (2006.01)

(56) References Cited

U.S. PATENT DOCUMENTS

| | | |
|---|---|---|
| 5,061,255 A | 10/1991 | Greenfeld et al. |
| 5,168,593 A | 12/1992 | Poje et al. |
| 5,240,675 A | 8/1993 | Wilk et al. |
| 5,584,314 A | 12/1996 | Bron |
| 7,854,728 B2 | 12/2010 | Boyle, Jr. |
| 2003/0109837 A1 | 6/2003 | McBride-Sakal |
| 2006/0264988 A1 | 11/2006 | Boyle |
| 2008/0208083 A1 | 8/2008 | Lin et al. |

OTHER PUBLICATIONS

Translation of Office Action of the Japanese Patent Office, dated Mar. 3, 2015, in corresponding Japanese patent application No. JP2013-514840.

SELF CLEANING SHUNT

RELATED APPLICATIONS

This application is a national phase application filed under 35 USC §371 of PCT Application No. PCT/IL2011/000486 with an International filing date of Jun. 19, 2011 which claims the benefit of U.S. Provisional Application No. 61/344,251, filed Jun. 18, 2010. Each of these applications is herein incorporated by reference in their entirety for all purposes.

FIELD OF THE INVENTION

The present invention relates to a self-cleaning inlet for a fluid shunt, especially for draining cerebrospinal fluid (CSF), as used in the treatment of hydrocephalus.

BACKGROUND OF THE INVENTION

Shunts are often used as internal medical devices to drain aberrant fluids from different organs. Reference is first made to FIG. 1, which illustrates a CSF shunt, implanted into the cranial cavity of a child. The shunt head 10, shown on a larger scale in FIG. 2, consists of a hollow catheter 20, usually made of silicone, with a series of perforations 21, 22, along its length, the holes often having different sizes and different spacings, such that fluid accumulated round the shunt can drain through the holes into the tube, and away from the region from which the fluid has to be drained. The excess fluid is generally drained into a body cavity such as the abdomen. The shunt head may have length calibrations imprinted thereon, so that the physician can estimate how far it has been inserted into the cranial cavity. The shunt head is attached by means of a tubular connector 18 to a drain tube 12, which conveys the excess cerebral fluids typically into the patient's abdomen. The drain tube is generally implanted just beneath the skin, with access to the cranial region to be drained and into the abdominal cavity being achieved by means of small incisions 16 in the meninges and the peritoneum respectively. In order to allow the patient to grow from infanthood without the need for changing the shunt, the end section of the drain tube 14 may be bundled up in the abdominal cavity, so that it can unravel as the child grows. Although CSF shunts are perhaps the most commonly used shunts, it is to be understood that such shunts could be applied to any other part of the body where the drainage of excess fluid is required, such as in urethral catheters, vesicostomy, peritoneal dialysis, and others. Furthermore, such shunts could also be used in industrial applications where it may be necessary to drain fluids from a remote inaccessible location.

Such prior art simple shunts generally have two major problems:
  (i) the inlet apertures might get clogged, and
  (ii) it may become infected.

When the shunt is clogged, an attempt to remove it from the body by surgery should be made. In cases where it is impossible to remove, another shunt may be placed in parallel to the malfunctioning one. When the shunt is infected it must be removed from the body by surgery. Surgeries of this kind are often high risk procedures.

The simple prior art shunt shown in FIGS. 1 and 2 have a significant drawback in that after some period of time inside the human body, living tissue growth may result in blockage of the holes by the tissue. This tissue is generally the main cause of shunt blockage. When trying to withdraw the shunt by surgery, the ingrown tissue may tear, causing intraventricular bleeding, which might be life threatening.

To avoid the risk of such bleeding, doctors sometimes prefer not to remove the shunt but to implant another one in addition to the original damaged or clogged one. This procedure includes surgery and the new shunt might also cause an infection. When a shunt is infected, it must be removed before any new device is inserted. In such a case, if the silicone tube needs to be removed, and if it is stuck to the choroid plexus, an open craniotomy and intraventricular operation needs to be performed in order to prevent intraventricular bleeding.

In order to avoid such complications, a number of self cleaning shunt heads have been proposed in the prior art. Many depend on back-flushing of the shunt head using the fluid within the tube. One such prior art shunt is shown in U.S. Pat. No. 5,584,314 to D. Bron, for "Self cleaning inlet head for a fluid." The head is cleaned by manually pressing on a reservoir implanted subcutaneously thus causing a cleaning motion by means of the shunt fluid. However, the head of this shunt appears to be mechanically complex, which may result in reduced reliability in the long term.

In co-pending International Patent Application No. WO2008/126087 for "Vibrating Robotic Crawler", having one co-inventor with the present application, there is described an autonomous vibration driven device, for motion through a lumen utilizing an array of flexible fibers attached to the body of the device. In that publication, there is described one application of such a device for keeping the bore of shunts clear of obstructions. The vibrating robotic crawler is capable of crawling in tubes, and is ideal for opening occlusions in such shunts, often preventing the need for shunt revision procedures.

However, it does not relate to the problem of the blocking of the shunt fluid inlet holes themselves, which may become blocked by the ingrowth of living tissue, such as choroid plexus or by blood clots.

The disclosures of each of the publications mentioned in this section and in other sections of the specification, are hereby incorporated by reference, each in its entirety.

SUMMARY OF THE INVENTION

The self cleaning shunt head comprises two components which operate co-operatively. The distal end of the shunt head is in the form of a tube having openings for draining the excess fluid, and this tube replaces the perforated end of the original shunt head. Inside this tube, there is disposed an internal elongate cleaning element, which may conveniently be constructed of a central shaft with bristles protruding therefrom, which can penetrate the tube drain openings. The cleaning element resembles a long brush. The element or its bristles can be vibrated, such that the bristles generate a cleaning action inside the openings, cleaning out any debris or clotted blood found in them, and preventing living tissue from growing into them. The openings can be in the form of holes or slots, and are most advantageously arranged in a predetermined array. The positions of the bristles on the cleaning element should be arranged with a similar array pitch and angular positioning, such that the bristles are correctly positioned to enter the openings when cleaning element and tube are correctly aligned. The correct radial alignment may be achieved by any simple mechanical method, such as a keyway. The vibration can be effected by any method which enables remote vibration to be effected. A particularly simple method is to incorporate a ferromagnetic or even a magnetic element within the cleaning element, and to cause these to vibrate by means of an externally applied field magnetic field. As an alternative to vibrating the entire cleaning brush, the bristles could be manufactured of a ferromagnetic or magnetic material, such that they alone vibrate. Another alternative is use of an appropriate ultrasound field applied externally, causing the bristles to vibrate.

Even in case of an infection, use of this shunt head makes it simpler to remove the shunt from the body without the risk of life-threatening internal bleeding, since the absence of living tissue inside the shunt holes makes withdrawal of the shunt less hazardous. In the event that no infections occur, the self cleaning shunt should be suitable for life time use.

There is thus provided in accordance with an exemplary implementation of the devices described in this disclosure, a fluid inlet head for use on a shunt, the head comprising:
(i) a first tube having a set of openings disposed in its wall, and
(ii) a cleaning element comprising a central shaft with a number of bristles protruding
therefrom such that when the cleaning element is installed within the first tube, at least some of the bristles can enter the openings,
wherein the cleaning element is adapted to vibrate when subjected to a vibration generating system, such that the bristles can move within the openings.

In such a fluid inlet head, the first tube may be essentially cylindrical. Furthermore, the openings may be disposed in predetermined lateral and radial positions in the tube wall, and the bristles may protrude from the cleaning element in lateral and radial locations substantially aligned with the lateral and radial positions of the openings in the wall of the first tube. In any of the above described heads, the bristles may be attached to a central shaft of the cleaning element.

Additional implementations can include a fluid inlet head as described above, wherein the vibration generating system comprises an external field which operates on the cleaning element. In such a case, the external field may be an alternating magnetic field, and the cleaning element then should comprise at least one of a magnetic material and a magnetized material. In that situation, the shaft may be constructed of either one of a magnetic material and a magnetized material, and/or at least some of the bristles may be constructed of either one of a magnetic material and a magnetized material.

As an alternative to such fields, the vibration generating system may comprise an externally applied ultrasonic field having a frequency in the range of the mechanical self-resonant frequency of at least some of the bristles.

As an alternative to use of an external applied field, the vibration generating system in other exemplary implementation may be a vibration transducer disposed on the cleaning element, and could be any one of a mechanical, electromagnetic, or piezoelectric transducer, or another suitable type.

Additionally, alternative implementations of any of the above-described heads may further have bristles of length such that they do not protrude substantially through the openings beyond the outer wall of the first tube.

Furthermore, other exemplary implementations of the fluid inlet head for use on a shunt may further comprise a second tube having a set of openings, at least some of which are disposed in the wall of the second tube in the same predetermined lateral and radial locations as those of the first tube, the second tube being installed inside the first tube, such that when the tubes are not aligned with their sets of openings mutually lined up, the bristles on the cleaning element cannot protrude into the openings in the first cylindrical tube. Such implementations should also comprise a mechanism for changing the alignment of the first and second tubes, such that the sets of openings can be mutually lined up only after installation of the fluid inlet head.

Yet other implementations perform a method of maintaining clear the openings of a fluid inlet head for use on a shunt, comprising:
(i) providing a fluid inlet head for use on the shunt, the head comprising a first tube having a set of openings disposed in its wall and a cleaning element comprising a central shaft with a number of bristles protruding therefrom, such that when the cleaning element is installed within the first tube, at least some of the bristles can enter the openings, and
(ii) vibrating the cleaning element such that the bristles can move within the openings, thereby maintaining them clear.

In such a method, the vibrating may be performed using an external field which operates on the cleaning element. The external field may be an alternating magnetic field, and the cleaning element should then comprise at least one of a magnetic material and a magnetized material. Alternatively, the shaft may be constructed of either one of a magnetic material and a magnetized material, or at least some of the bristles may be constructed of either one of a magnetic material and a magnetized material.

As an alternative, the externally applied field may be an ultrasound field having a frequency in the range of the mechanical self-resonant frequency of at least some of the bristles.

In some other exemplary implementations of these methods, the cleaning element may further comprise a vibration transducer, and the vibration is performed by actuating the vibration transducer. Such a vibration transducer may be any one of a mechanical, electromagnetic, or piezoelectric transducer.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
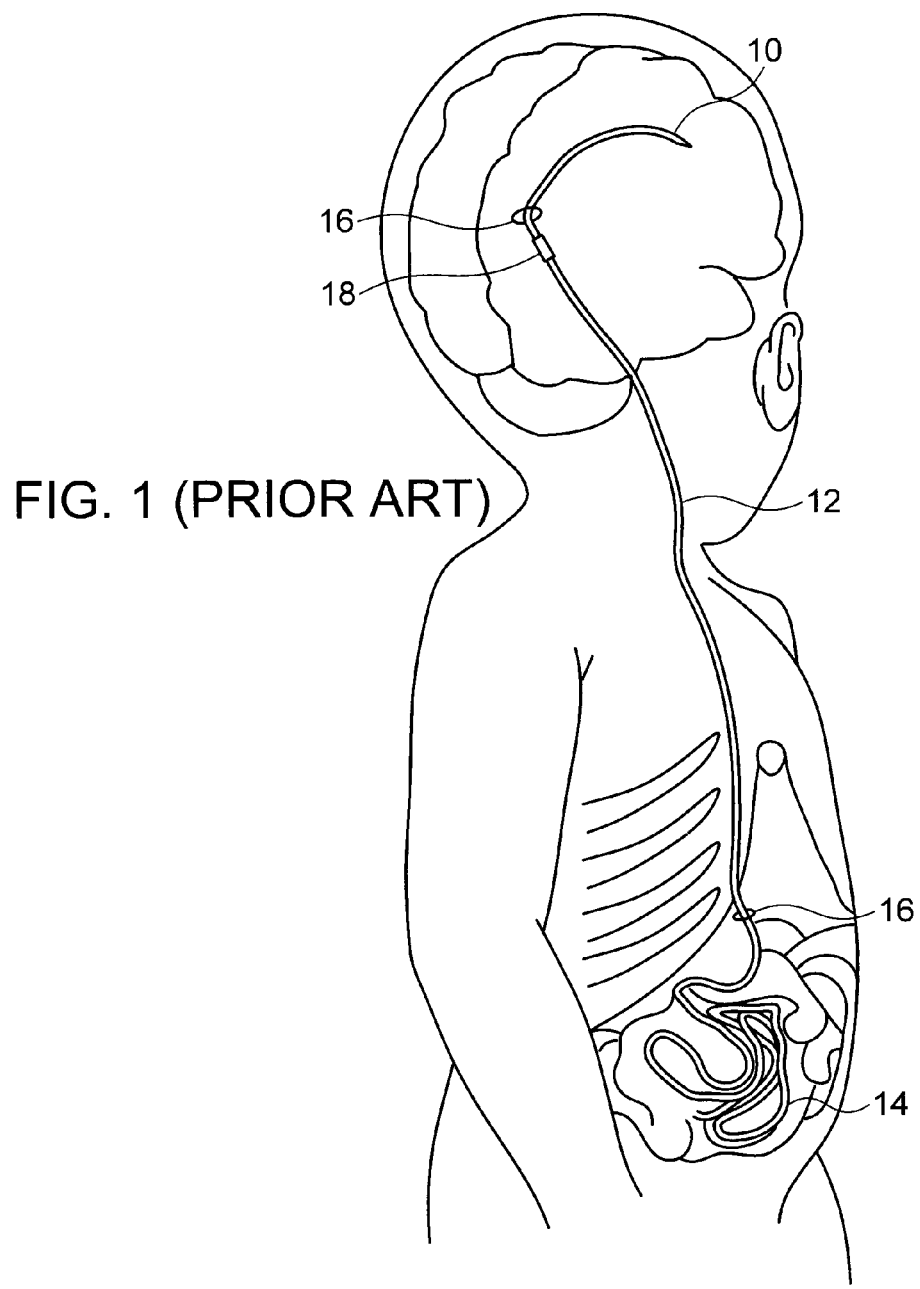
FIG. 1 illustrates a prior art CSF shunt system, implanted into the cranial cavity of a child.
Figure 2:
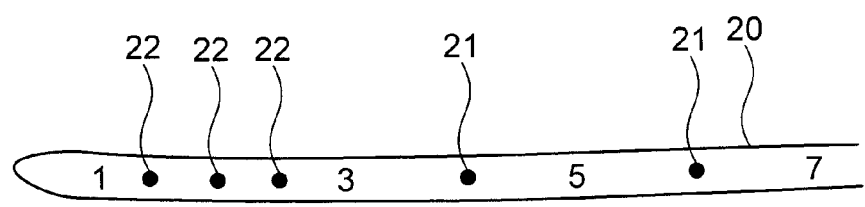
FIG. 2 shows schematically a prior art shunt head.
Figure 3:
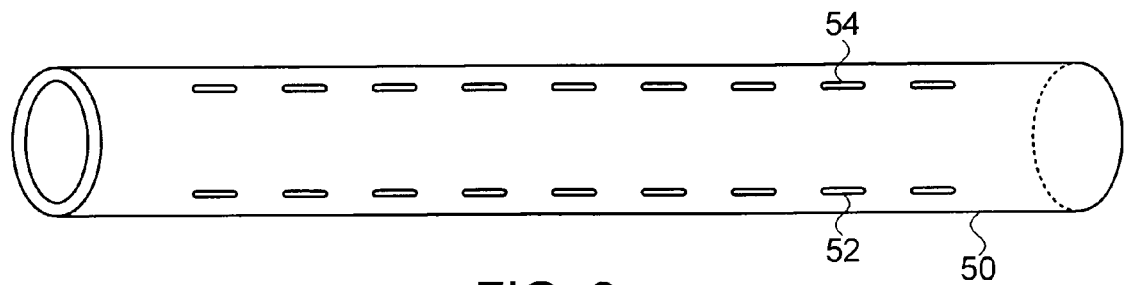
FIG. 3 illustrates schematically an exemplary tube element suitable for use at the distal end of the shunt.

Reference is now made to FIG. 3, which illustrates schematically an example of a tube element 50 suitable for use at the distal end of the shunt. In the example shown in FIG. 3, the fluid draining openings are arranged in arrays of slots down the length of the tube, each array being positioned at a different angular position around the circumference of the tube. In the example shown in FIG. 3, two visible rows of slots 52, 54 are shown arranged at angularly orthogonal positions relative to each other, but such a tube may typically have four such rows, arranged at 90° to each other, or any other number of rows of openings. Furthermore, although the tube is shown having an essentially cylindrical profile, this being the most convenient shape to manufacturer, tubes with other sectional profile shapes can also be used in this application.

Figure 4A:
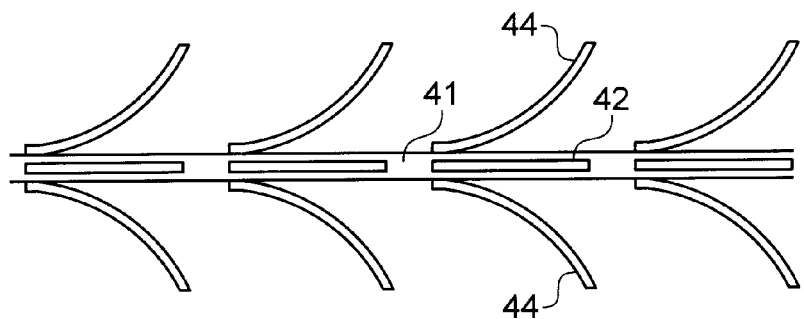
FIGS. 4A and 4B are two schematic views of a cleaning element adapted for use with the drain tube element of FIG. 3.
Figure 4B:
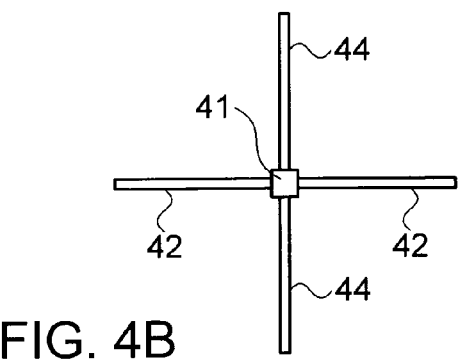

Reference is now made to FIGS. 4A and 4B, which illustrate schematically a cleaning element adapted for use with the drain tube of FIG. 3. FIG. 4A is a side view of the cleaning element, while FIG. 4B is an end view thereof. The cleaner element has a central shaft 41 with a number of bristles 42, 44 attached thereto. The bristles are preferably located longitudinally along the shaft such that the distance between successive bristles is the same as the distance between successive openings in the tube. Likewise they should preferably be located radially around the shaft at the same angular intervals as the openings in the tube. In the example shown in FIGS. 4A and 4B, four radial sets of bristles are shown located at right angles to each other. The arrangement of bristles should be such that when the cleaner is positioned correctly, the bristles are located opposite the openings in the tube.

Figure 5:
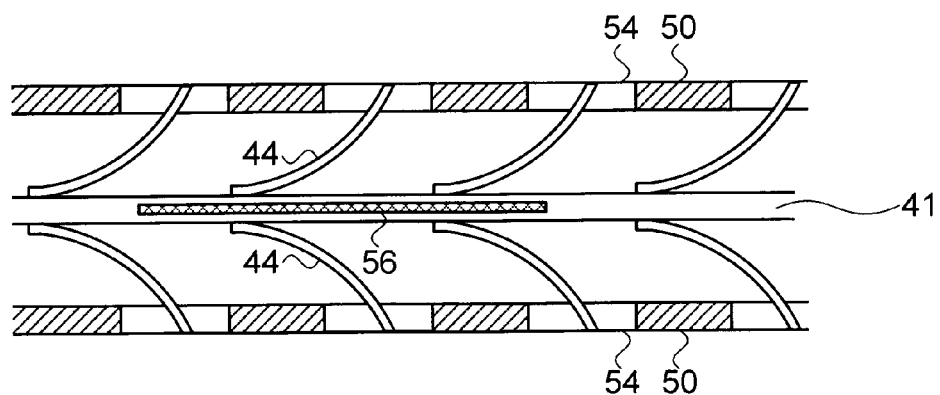
FIG. 5 is a cutaway drawing of the completely assembled self-cleaning shunt head of the present application.
Figure 6:
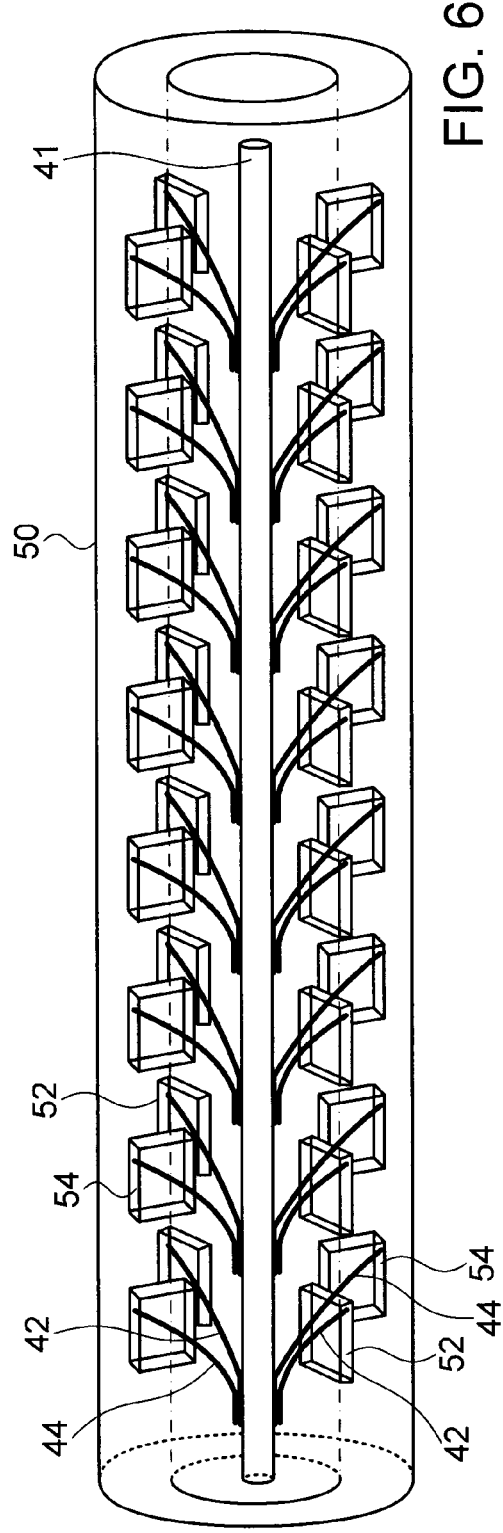
FIG. 6 is an "X-ray" isometric drawing of the complete head shown in FIG. 5.

Reference is now made to FIGS. 5 and 6, each illustrating the completely assembled self-cleaning shunt head. FIG. 5 is a cutaway drawing of the head, while FIG. 6 is an "X-ray" isometric drawing of the head. In FIG. 5, the bristles 44 are shown protruding into the slots 54. In the isometric drawing of FIG. 6, both orthogonal sets of bristles are shown protruding into their respective slots. Bristles 44 extend in the vertical direction of the drawing upwards and downwards into the slots 54, while bristles 42 extended in the horizontal direction of the drawing sideways into the slots 52.

In order for the bristles to perform their cleaning action, the cleaning element must be vibrated. One particularly simple way of achieving such vibration is by having one or more onboard magnets or ferromagnetic slugs attached to the cleaner shaft, or by making the cleaner shaft itself of a magnetic or magnetized material, and applying an external alternating magnetic field by means of a coil or a vibrating permanent magnet, that will influence the small magnet(s) or ferromagnetic element on the cleaner element and cause vibrations thereof. This implementation enables unlimited operation time, since the activation energy for generating the vibration is provided externally and is not dependent on the use of onboard batteries, while also maintaining simplicity of operation. The applied field direction may be such that the cleaning element vibrates along its length, or in any other direction other than axial which causes the bristles to penetrate the slot openings, or in any combination of such motions. Thus, for example, since the shaft diameter may be small compared with the internal diameter of the tube, sufficient clearance can be provided for the cleaner element to vibrate in a rotation motion around axes perpendicular to the axis of the tube, such that the cleaner performs a see-saw type of motion, with bristles at opposite ends penetrating slots at opposite sides of the tube. In general, the vibratory motion generation system should be such as to reduce as much as possible sensitivity to direction of the externally applied field, so as not to restrict the positioning of the patient when the cleaning procedure is activated. Entry of bristles into the slots in any manner which results in successful clearance of the slots may be advantageous.

As an alternative to causing the shaft to vibrate, it is possible to generate the vibrations directly in the fibers, such as by making them of a magnetized or a magnetic material and applying an external alternating magnetic field, or by any other suitable method. The external field can be applied from outside of the subject's body in which the shunt is installed.

An alternative method of generating the vibrations could be by use of an ultrasound signal applied externally at a frequency related to the mechanical self-resonant frequency of the bristles, such that they vibrate when the field is applied.

The vibrations must be of such magnitude and direction that the bristles vibrate within the openings in the tube. Optimally, the bristles should penetrate the slots to their full depth, so that no tissue growth or blockage can occur at any depth in the slots. Limiting the extension outside the tube may be advisable in order to avoid injury to tissues around the tube, though some penetration outside the tube may be allowable. There may be several slots in different directions so that the cleaning process can be made less sensitive to the direction of the applied external field.

It is also possible to have an on-board vibration generator 56 mounted on the cleaning element, such as is shown schematically in FIG. 5. Operation of the cleaning process can then be simpler, as there is no need to activate any external influence, but rather the cleaning is done autonomously. The on-board power supply may be long-lasting, or may be capable of being charged by an external power supply. The on-board vibration generator can be a mechanical transducer, such as by means of an eccentric or stepped rotating element, a magnetic transducer or a piezoelectric transducer, or any other form of vibration generator. The internal battery can be recharged when necessary by means of an externally applied induced field, as is known in the art. As an alternative to the use of an on-board battery, the vibration transducer can be provided with leads to an external power connector, and the vibration transducer powered directly by connection of an external power source to the connector when the cleaning procedure is to be activated.

In use, the tube with the openings is installed on the end of the shunt catheter before installation, with the cleaner inside. The combination cleaner element and tube are attached to a regular shunt tube instead of its punctured segment. The final result looks similar to the original shunt in shape and size, except that the punctured segment has been replaced by the tube and bristled cleaner. As an alternative, the cleaner may be embedded within the original shunt head tube. As an alternative, the cleaner element can be installed once the shunt is in position. At predetermined intervals the cleaner is vibrated in order to ensure that the openings remain clear of ingrowing tissue.

The movement of the cleaning element inside the tube depends on the alignment of the magnet and the amplitude and frequency of the magnetic field generated by the external source (using the example of a magnetic field driven application). The motion generated may be such that the bristles can generally move in two ways:
(i) Forward and backward inside the tube slots, by axial motion.
(ii) Inside and outside the tube slots by radial or rotational motion
or a combination of both. By its movement, the cleaner changes the hydrodynamic flow pattern inside the slots, making it impossible for tissue to grow near and inside the openings, and preventing living tissue from growing inside the slots. In addition, the bristles themselves can mechanically clean out any tissue which begins to form in the openings between cleaning sessions.

Figure 7:
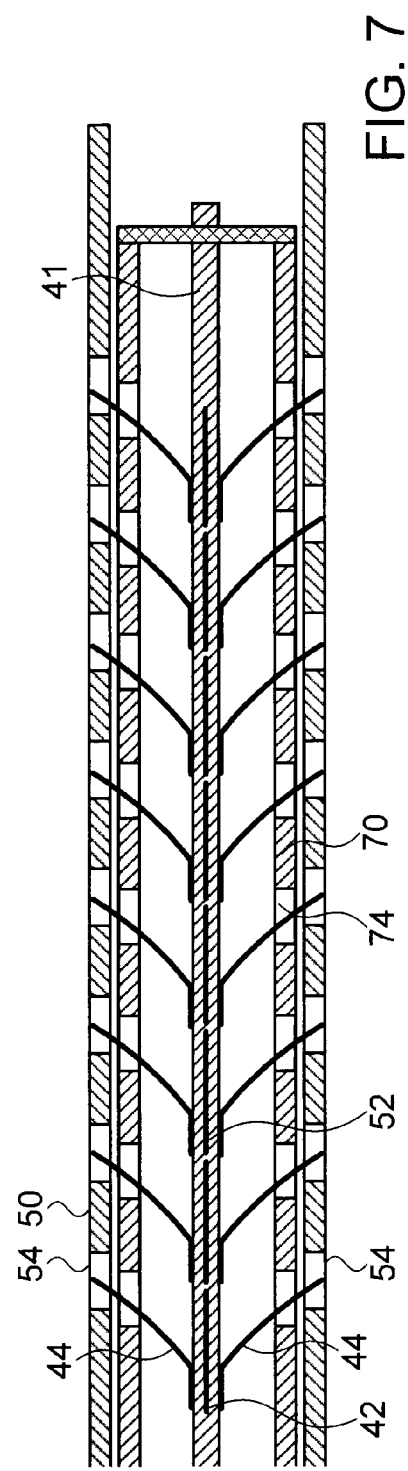
FIG. 7 illustrates schematically a further implementation of the device of FIGS. 5 and 6, utilizing a second cylindrical tube for preventing the bristles from projecting from the head when installing it.

Reference is now made to FIG. 7, which illustrates a further implementation of the present device, utilizing a second cylindrical tube 70 whose operation adds a safety factor when installing the device. The second tube 70 fits concentrically inside the first tube 50, and has a series of openings 74 in essentially the same positions as the openings in the outer tube. In order to prevent the bristles from sticking into surrounding tissue during installation of the shunt, the two concentric tubes are arranged to be aligned such that the openings are not opposite each other during insertion, such that the bristles are prevented from protruding from the outer tube and causing possible damage to surrounding tissue. Once the head of the shunt is installed into its desired position, the inner tube can be moved such that the openings of the inner and outer tube are now aligned, and the bristles can pass into the openings to perform their cleaning action. This movement can be generated by means of a simple mechanical motion imparted by the installation device once final location has been confirmed. The mutual motion of the inner and outer tubes is most conveniently performed in a lateral direction, though a rotational movement may also be used. In the drawing of FIG. 7, the openings are shown in their open aligned positions, during normal use after installation, so that the bristles can operate correctly in keeping the openings clear.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A fluid inlet head for use on a shunt, comprising:
   a first tube having a set of openings disposed in its wall; and
   a cleaning element comprising a central shaft with a number of bristles protruding therefrom such that when said cleaning element is installed within said first tube, at least some of said bristles can enter said openings;
   wherein said cleaning element is adapted to vibrate when subjected to a vibration generating system, such that said bristles can move within said openings; and
   wherein said openings are disposed in predetermined lateral and radial positions in said first tube wall, and said bristles protrude from said cleaning element in lateral and radial locations substantially aligned with the lateral and radial positions of said openings in the wall of said first tube.

2. A fluid inlet head for use on a shunt, according to claim 1, wherein said first tube is essentially cylindrical.

3. A fluid inlet head for use on a shunt, according to 1, wherein said bristles are attached to a central shaft of said cleaning element.

4. A fluid inlet head for use on a shunt, according to claim 1, wherein said vibration generating system generates an external field which operates on said cleaning element.

5. A fluid inlet head for use on a shunt, according to claim 4, wherein said external field is an alternating magnetic field, and said cleaning element comprises at least one of a magnetic material and a magnetized material.

6. A fluid inlet head for use on a shunt, according to claim 5, wherein said shaft is constructed of either one of a magnetic material and a magnetized material.

7. A fluid inlet head for use on a shunt, according to claim 5 wherein at least some of said bristles are constructed of either one of a magnetic material and a magnetized material.

8. A fluid inlet head for use on a shunt, according to claim 1, wherein said vibration generating system is a vibration transducer disposed on said cleaning element.

9. A fluid inlet head for use on a shunt, according to claim 1, wherein the vibration generating system comprises an externally applied ultrasound field having a frequency in the range of the mechanical self-resonant frequency of at least some of the bristles.

10. A fluid inlet head for use on a shunt, according to claim 1, wherein the length of said bristles is such that they do not protrude substantially through said openings beyond the outer wall of said first tube.

11. A fluid inlet head for use on a shunt according to claim 1, further comprising a second tube having a set of openings, at least some of which are disposed in its wall in the same predetermined lateral and radial locations as those of said first tube, said second tube being installed inside said first tube, such that when said tubes are not aligned with said sets of openings mutually lined up, the bristles on said cleaning element cannot protrude into said openings in said first tube.

12. A fluid inlet head for use on a shunt, according to claim 11, further comprising a mechanism for changing the alignment of said first and second tubes, such that said sets of openings can be mutually lined up only after installation of said fluid inlet head.

* * * * *